United States Patent
Fitzgerald et al.

(10) Patent No.: US 6,881,572 B2
(45) Date of Patent: Apr. 19, 2005

(54) ASSAY DEVICE INCUBATOR

(75) Inventors: Stephen Peter Fitzgerald, Co. Antrim (GB); John Victor Lamont, Co. Antrim (GB); Robert Ivan McConnell, Co. Antrim (GB)

(73) Assignee: Randox Laboratories Limited, Co. Antrim (GB)

( * ) Notice: Subject to any disclaimer, the term of this patent is extended or adjusted under 35 U.S.C. 154(b) by 194 days.

(21) Appl. No.: 10/406,224

(22) Filed: Apr. 4, 2003

(65) Prior Publication Data
US 2003/0215367 A1 Nov. 20, 2003

(30) Foreign Application Priority Data
Apr. 19, 2002 (GB) .............................................. 0209025

(51) Int. Cl.⁷ ................................................ C12M 1/02
(52) U.S. Cl. ..................... 435/303.3; 435/809; 422/104
(58) Field of Search ............................. 435/303.3, 809; 422/104; 312/35, 42, 50, 236

(56) References Cited
U.S. PATENT DOCUMENTS 3,576,721 A * 4/1971 Mason .................... 435/303.3
5,470,744 A * 11/1995 Astle ....................... 435/286.7
5,577,837 A    11/1996 Martin et al.
6,050,719 A * 4/2000 Winkler et al. ............. 366/144
6,475,776 B1 * 11/2002 Higuchi .................... 435/303.3
6,649,128 B1 * 11/2003 Meyer et al. ................. 422/63
6,753,178 B1 * 6/2004 Adelberg et al. ........... 435/261

FOREIGN PATENT DOCUMENTS

DE    197 13 993 A1    5/1998
EP    0 569 214 A2    11/1993
EP    0994 355 A1    4/2000
GB    1 434 422    5/1976

* cited by examiner

*Primary Examiner*—David A. Redding
(74) *Attorney, Agent, or Firm*—Oliff & Berridge PLC

(57) ABSTRACT

An assay device incubator comprises a housing (46) defining a region within which at least one assay device is located in use, the housing defining laterally opposed sidewalls (48, 50) of at least one bay (33) in which an assay device can be located. The housing (46) includes one or more guides (49, 51) for supporting the assay device and enabling the assay device to undergo to and fro movement therealong. A vibration system (40, 60) is coupled to the at least one tray in use for vibrating the tray to and fro along the or each guide. A heating system (70) heats the region within the housing.

9 Claims, 6 Drawing Sheets

ASSAY DEVICE INCUBATOR

FIELD OF THE INVENTION

The invention relates to an assay device incubator.

DESCRIPTION OF THE PRIOR ART

Assay devices are typically in the form of chips on which have been deposited an array of localised reactive sites containing different reactive species, for example different antibodies.

In this context, "assay" means the quantitative analysis of a substance to determine the proportion of some valuable or potent constituent e.g. the active constituent in a pharmaceutical.

An immunoassay is a technique which measures the presence of a substance (analyte) in a biological sample exploiting an immunological reaction between antibody and antigen.

In the fields of chemical/veterinary diagnosis or drug screening, it is necessary to analyse samples to determine the presence of certain analytes. Recently, it has been proposed to provide a set of different antibodies on respective reactive sites on a substrate such as a chip. The sample is deposited on the chip and following incubation and other processes, a chemiluminescence process is monitored to detect the presence or absence of the appropriate analyte at each site. This is described in more detail in EP-A-0902394.

One process which is typically performed on an assay device is incubation in which the temperature of the assay device is raised to a predetermined value, for example 37° C. and during incubation the assay device is shaken or vibrated to create liquid motion so as to speed up and optimise the binding assay reactions necessary for analyser operation.

We have described one example of an incubator/shaker in EP-A-0994355 but this has a fairly complex structure.

EP-A-0569214 describes an incubator in which the individual planes are supported on rotatable shafts, which on rotation, cause the planes to move slowly in their plane.

SUMMARY OF THE INVENTION

In accordance with the present invention, an assay device incubator comprises a housing defining a region within which at least one assay device is located in use, the housing defining laterally opposed sidewalls of at least one bay in which an assay device can be located, the housing including one or more guides for supporting the assay device and enabling the assay device to undergo to and fro movement therealong; a vibration system coupled to the at least one tray in use for vibrating the tray to and fro along the or each guide; and a heating system for heating the region within the housing In this new incubator, the heated part of the incubator, particularly the housing, remains stationary during the vibrational operation. This simplifies the structure of the incubator. In addition, the assay devices are supported primarily by the housing and not by the vibration system as in EP-A-0569214. This reduces strains on the vibration system and the mass vibrated.

Preferably, the housing defines a set of said bays within each of which an assay device can be located. In order to optimise heat distribution, each bay is preferably defined by heat conductive wall member(s).

The guide could comprise a surface, e.g. base plate, on which an assay device rests. Preferably, however, the housing defines for each bay a pair of sidewalls including respective guides for supporting the assay device In the preferred examples, each pair of guides comprises laterally spaced slots along which the assay devices or storage wells containing assay devices can be slid. The vibrational movement may also take place in the sliding direction or orthogonal to the sliding direction if the slots have sufficient depth.

Typically the heating system will be arranged to heat the entire region to a uniform temperature. However, in some cases more complex heating systems capable of independently heating individual bays could be implemented.

The vibration system conveniently includes a plate having a number of catches for attachment to respective assay device storage wells. Typically, these are balseal catches. In these examples, the assay devices are conveniently located in storage wells which are coupled directly or indirectly via storage trays with the support.

In other examples, the storage wells may be permanently fixed to the support, assay devices being inserted into and removed from the storage wells as required.

It is convenient, particularly when the incubator is used in an automatic processing assembly such as described in EP-A-0994355 to have a single assay device supply location. In those cases, conveniently the support and housing are jointly movable to align with the assay device supply location.

BRIEF DESCRIPTION OF THE DRAWINGS

An example of an assay device incubator will now be described with reference to the accompanying drawings, in which.

DESCRIPTION OF THE EMBODIMENT

Figure 1:
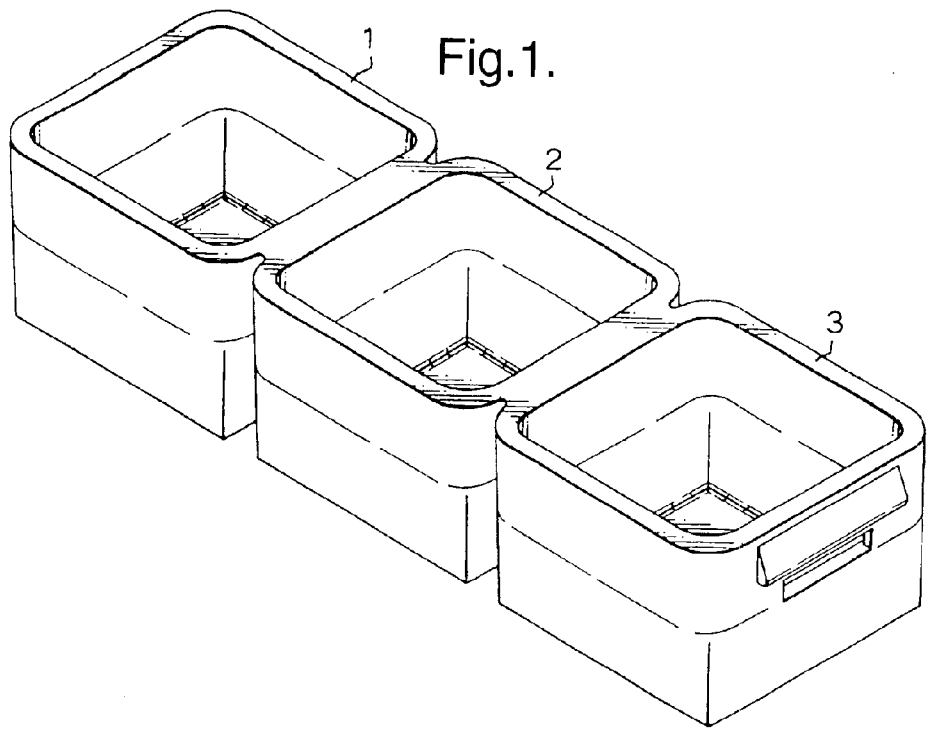
FIG. 1 is a perspective view of an array of storage wells.

The incubator to be described is designed to process assay device chips on which are deposited an array of localised reactive sites containing different antibodies. The chip is typically of ceramic or silicon. The chips are supplied "factory spotted" with an array of reactive species and for ease of handling are located in sets of integral storage wells 1–3 (FIG. 1) although individual wells could be used instead. Typically, the array of storage wells and chips is packaged for sending to a remote user. This is described in more detail in EP-A-0988893. For further ease of handling, the arrays of storage wells 1–3 are removably mounted in a carrying tray 20. This carrying tray (FIG. 2) is made of a plastics moulding and has two sets of crossbars 21,22 extending between opposite sidewalls 23,24 respectively. Nine openings 25 are defined into which the respective storage wells can be located. The tray 20 has a flange projection 26 on one side for connecting to a positioning device (not shown) and a protruding boss 27 on the opposite side. A pair of slide flanges 28 are provided on the other pair of sides 23. Each set of three storage wells 1–3 is loaded parallel to the crossbars 21 with the crossbars 22 entering between adjacent storage wells. The loaded carrier tray is then sealed in suitable packing materials for transportation. Preferably, the storage wells are left in place in the carrier tray and the tray used to move the storage wells about the immunoassay process. Alternatively, the storage wells can be supplied separately or removed from the carrier tray.

The user can decide whether to put one, two or three arrays of storage wells in the tray depending upon the number of samples to be tested.

The incubator shown in FIGS. 3 to 7 comprises a framework 30 mounted on rubber feet or dampers 80 to reduce transmission of vibration to other instruments. The framework 30 has a front wall 5 defining an access slot 34 and within which is mounted a processing assembly 31 shown in more detail in FIG. 4. The processing assembly is mounted for vertical movement under the control of a drive motor 32 so as to bring selected bays or rack slots 33 within the assembly 31 into alignment with the access slot 34.

The processing assembly 31 comprises a latch plate 40 having two sets of six vertically arranged balseal catches 41 aligned with respective bays 33. The plate 40 is bolted to a back plate 74 whose upper and lower ends are connected to upper and lower sliders 42,43 respectively which engage in respective slots 44,45 in a generally square shaped housing 46. This engagement allows the slide members 42,43 to slide to and fro along the slots 44,45 thus guiding corresponding movement of the plate 40 which the housing 46 remains stationary.

The housing 46 includes an outer insulating layer 47 surrounding an aluminium shell 48 which defines elongate slots 49 corresponding to each bay 33. An aluminium dividing wall 50 extends vertically between top and bottom portions of the aluminium shell 48 and defines corresponding slots 51 aligned with the slots 49.

Further aluminium dividing plates 52 extend across each bay 33 so as to separate the bays from one another.

By constructing the walls of the bays of a thermally conductive material (metal), a high degree of temperature uniformity across the bays is ensured.

The housing 46 is fixed to the framework 30 via a backplate 74.

Vibrational movement of the plate 40 is caused by a vibrator motor 60 mounted on a bracket 61 secured to the housing 46. The vibrator motor 60 is connected via an eccentric piece 62 (FIG. 7) to a crank arm 63 mounted at its other end in a bearing block 64 extending through a PCB 72 and bolted to the backplate 74. Thus, rotation of the motor 60 will cause to and fro movement of the plate 40. This movement is sensed by means of a stop flag 65 which rotates with the crank arm and a stop sensor 66 mounted on the bracket 61. Alternatively, a shaft encoder could be used.

A heating system 70 (not shown in detail) is formed by heating elements which are wrapped around the top, sides and bottom of the aluminium sections of the housing 46 under the insulation 47.

Figure 2:
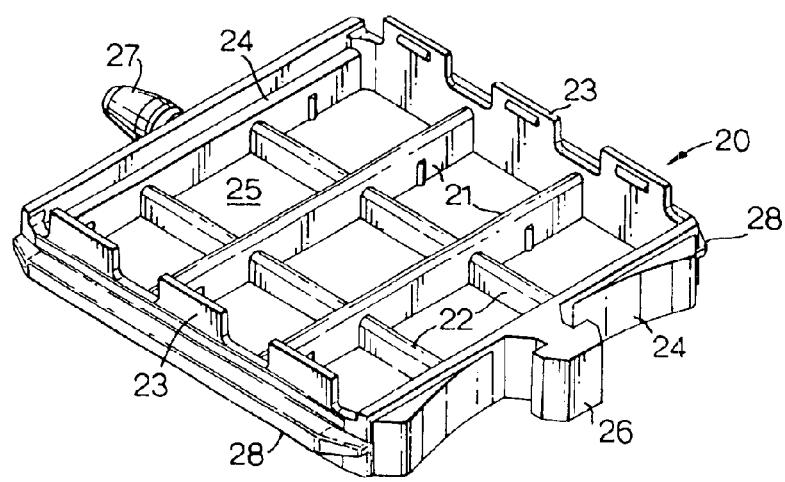
FIG. 2 is a perspective view of a carrying tray for the array of storage wells shown in FIG. 1.
Figure 3:
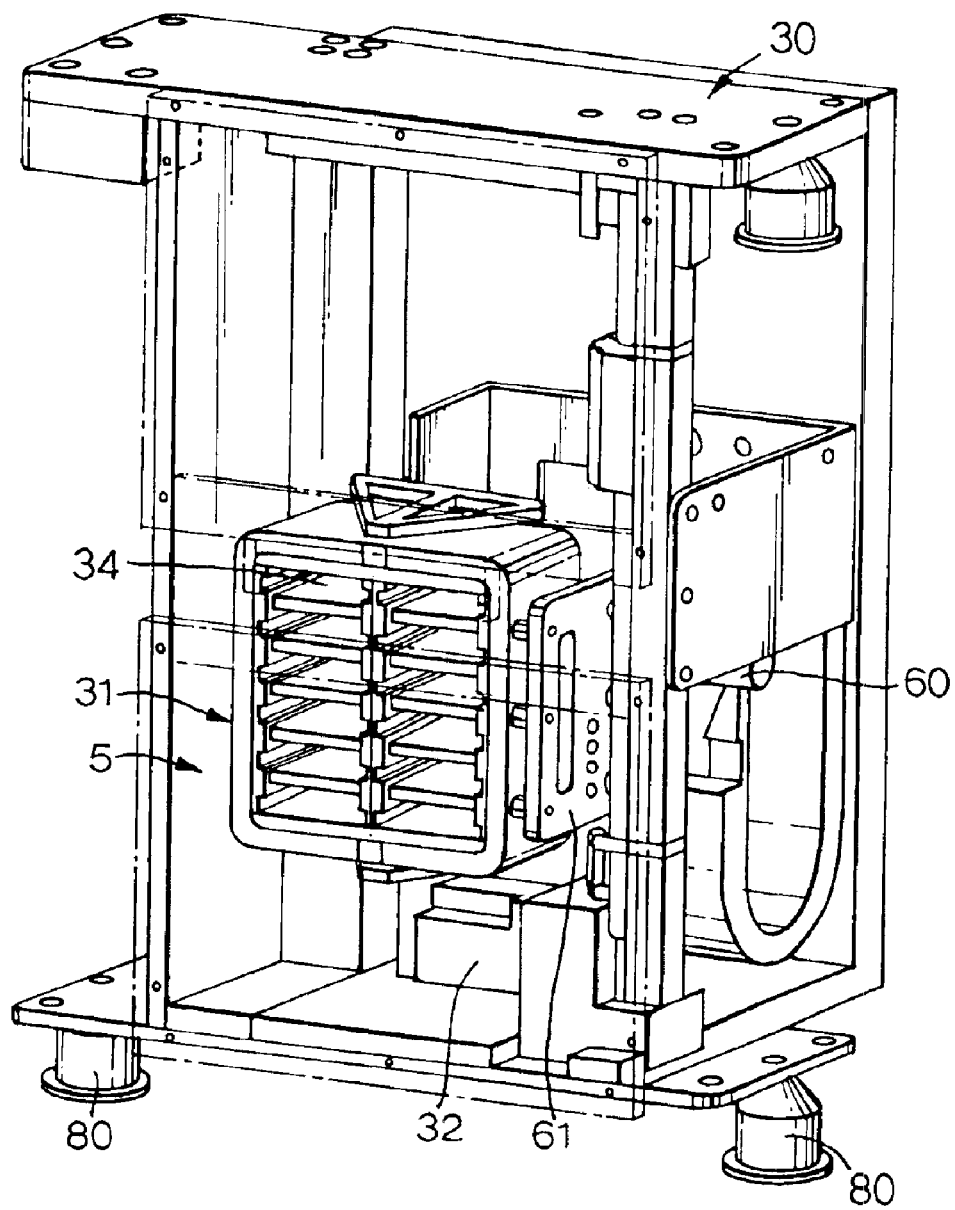
FIG. 3 is a perspective view of the incubator.
Figure 4:
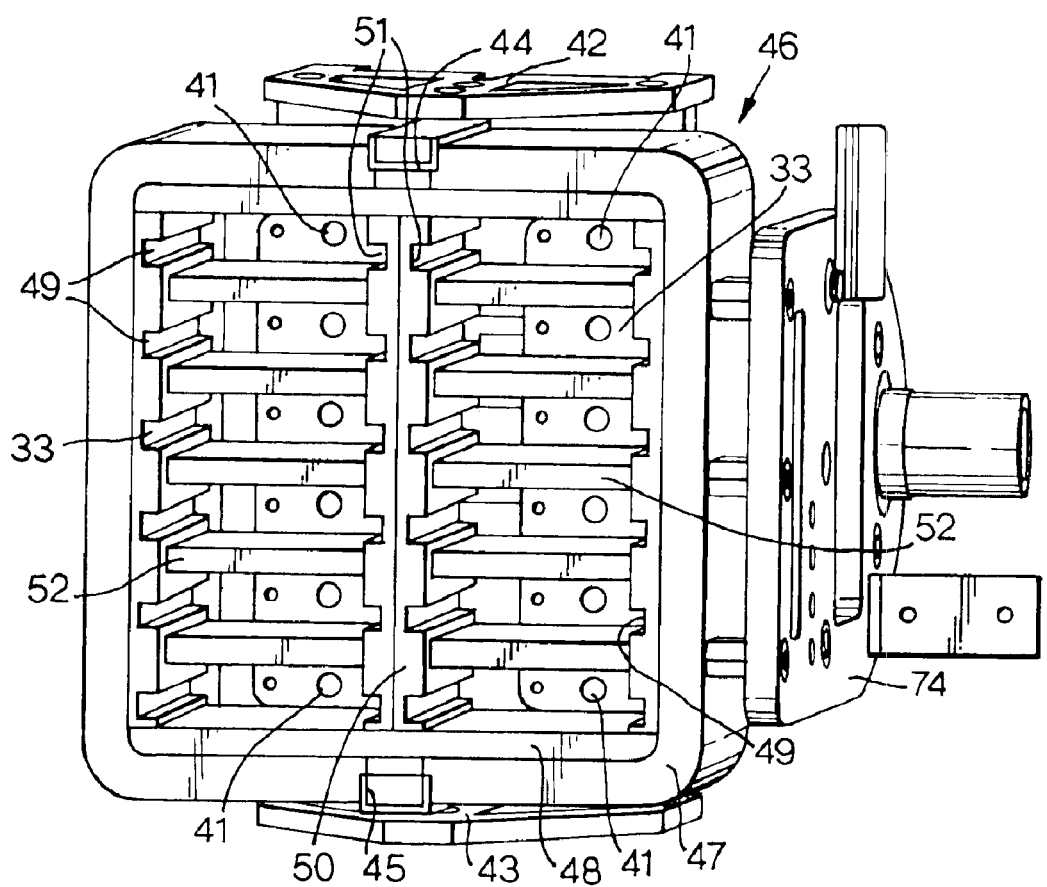
FIG. 4 is a front view of the support and housing.

In use, the heating system 70 is activated to heat the bays 33 to the desired temperature and storage trays 20 of the type shown in FIG. 2 containing storage wells and chips are loaded and unloaded in the rack slots or bays 33 by vertically moving the assembly 31 using the motor 32 to bring the appropriate bays 33 into alignment with the access slot 34.

Figure 5:
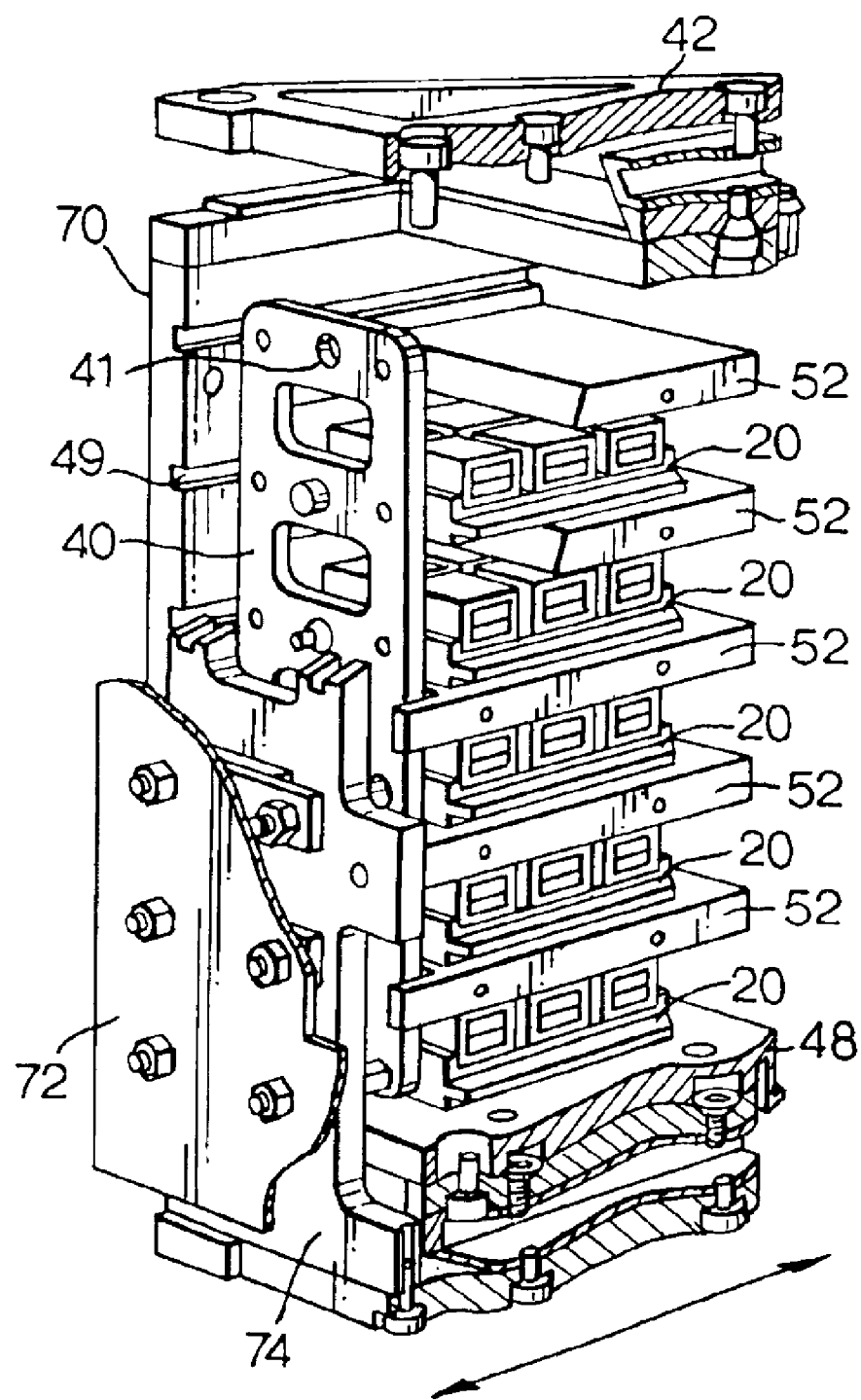
FIG. 5 is a perspective view, partly cut away, from behind of the support and related components but with the housing removed and showing storage trays in some of the bays.
Figure 6:
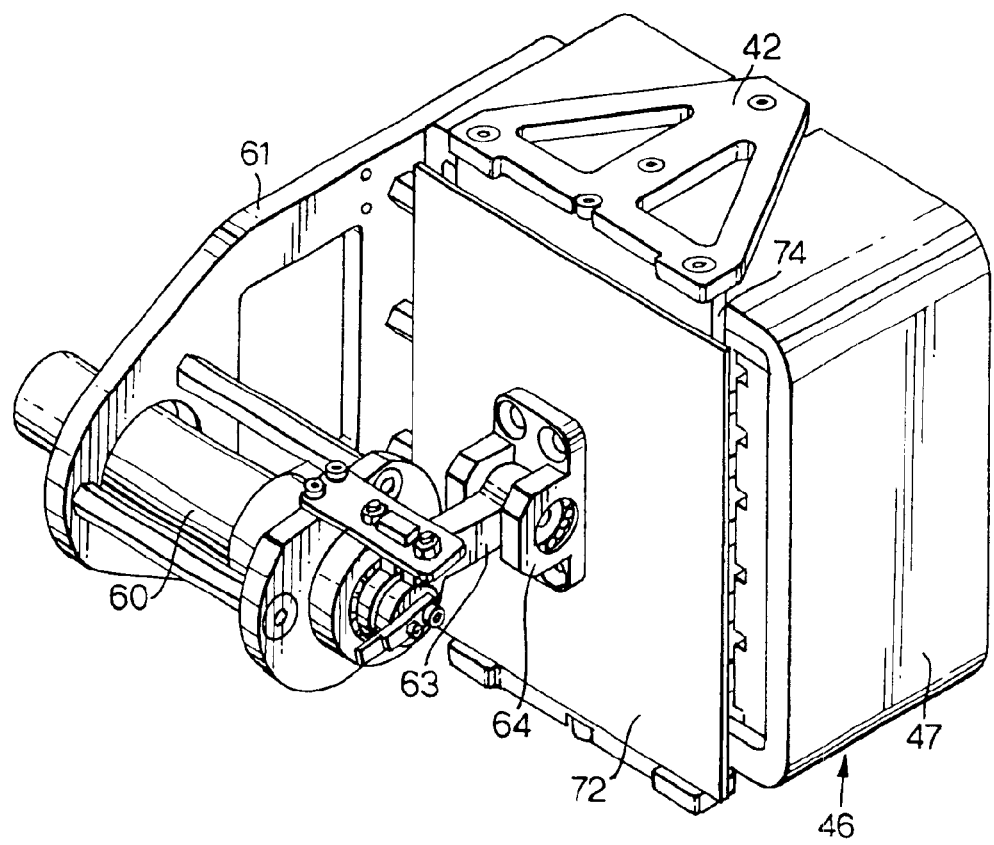
FIG. 6 illustrates the connection of the vibrator motor to the support plate; and, FIG. 7 illustrates the vibrator motor drive in more detail.
Figure 7:
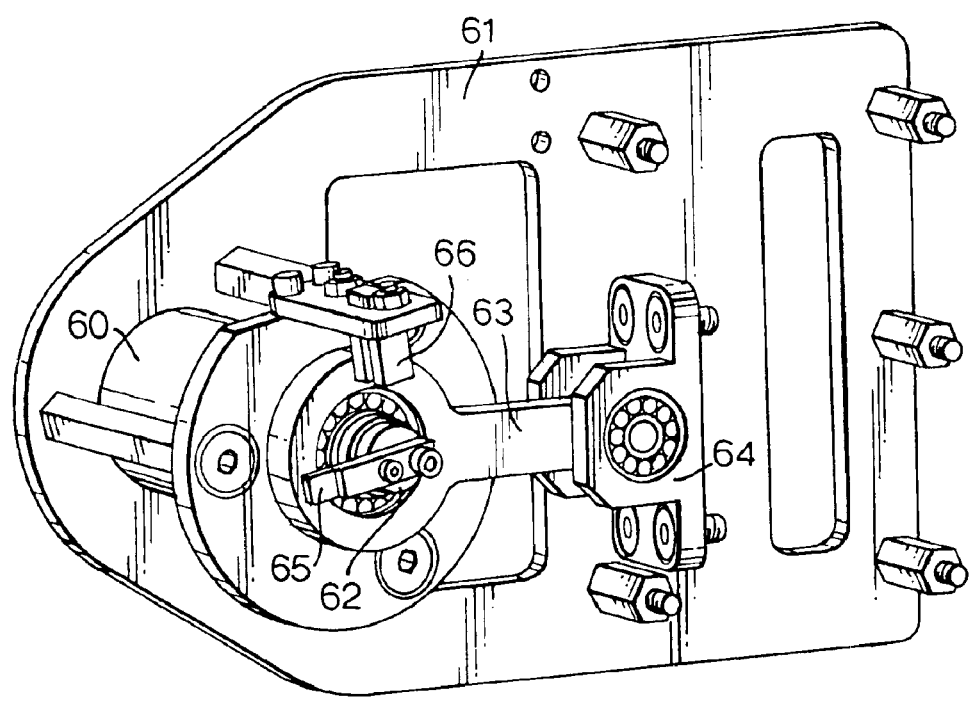

On loading, a tray 20 is inserted into a bay with flanges 28 received in slots 49, 51 until the boss 27 engages the balseal catch 41 (which is sensed). A number of mounted trays 20 are shown in FIG. 5. Each tray is supported by the respective pair of slots 49, 51.

It will be noted that the latch 41 to which the racks are attached by means of ballseals is not required to support the full weight of the racks because they slide on slots in the aluminium shell. Also lower drive motor requirements and/or higher frequency oscillation is possible with this design compared with known systems. The mass/inertia of the moving latch plate and racks is lower than that of complete housing which was vibrated in the earlier design.

The motor 60 is then activated and as the motor 60 rotates, the crank arm 63 moves the plate 40 to and fro thus achieving a vibration motion as shown by the arrows in FIG. 5. The stop flag 65 can be arranged to set a datum position for example for loading and unloading.

The shaking frequency and amplitude/stroke of the crank arm 63 are selected for the specific fluid volume within the well, the well shape and well dimensions/volume (and binding optimisation). This is required in order to provide the fluid flow and mixing within the well necessary to achieve uniformity of fluid interaction across the chip surface as well as to ensure that no fluid is ejected from the wells possibly resulting in fluid loss, cross contamination of wells and possible incorrect assay analysis.

The incubator bays are normally raised within the box 31 above the level of the access slot 34 for shaking/incubation and only lowered to allow for the periodic insertion/removal of each carrier (and its biochip wells) in turn. This ensures that the bays and carriers are only near the access slot for short periods where heat loss, due to eg air currents, could influence the temperature of adjacent biochip wells and the effectiveness of the incubation process.

The shaking stroke can be changed by replacement of the eccentric piece 62. The shaking frequency can be changed either by electronic adjustment or software control. The sinusoidal motion is inherent in the design of the eccentric drive (assuming a constant speed motor). The incubation time, i.e. time the biochips are in the incubator, is software controlled as part of the overall robotics cycle for the analyser and can be changed to meet particular assay requirements. Sensors (not shown) are included at each bay that detect the presence of the carrier (also termed rack) containing the biochip wells. Other temperature sensors (not shown) provide feedback for temperature control and monitoring. The sensors are all connected to the PCB 72.

We claim:

1. An assay device incubator comprising a housing defining a region within which at least one assay device is located in use, the housing defining laterally opposed sidewalls of at least one bay in which an assay device can be located, the housing including one or more guides for supporting the assay device and enabling the assay device to undergo to and fro movement therealong; a vibration system coupled to the at least one assay device in use for vibrating the assay device to and fro along the or each guide; and a heating system for heating the region within the housing.

2. An incubator according to claim 1, wherein the housing defines a set of said bays within each of which an assay device can be located.

3. An incubator according to claim 2, wherein the bays are defined by heat conductive side walls.

4. An incubator according to claim 1, wherein the housing defines for each bay a pair of sidewalls including respective guides for supporting the assay device.

5. An incubator according to claim 4, wherein each pair of guides comprises laterally opposed slots along which the assay devices can be slid.

6. An incubator according to claim 1, wherein the vibration system includes a plate movable in the vibration directions relative to the housing and having a number of catches for attachment to respective assay device storage wells.

7. An incubator according to claim 6, wherein the catches comprise balseal catches.

8. An incubator according to claim 6, wherein the plate and housing are jointly movable to align with an assay device supply location.

9. An incubator according to claim 8, wherein the joint movement is in a direction orthogonal to the vibration direction.

* * * * *